United States Patent [19]

Dürr et al.

[11] Patent Number: 5,382,125
[45] Date of Patent: Jan. 17, 1995

[54] SCREW UNIT

[76] Inventors: Walter Dürr, Panoramastrasse 5, D7537 Remchingen; Axel Kirsch, Talstrasse 23, D7024 Filderstradt, both of Germany

[21] Appl. No.: 971,862
[22] PCT Filed: Apr. 7, 1992
[86] PCT No.: PCT/DE92/00290
  § 371 Date: Jan. 13, 1993
  § 102(e) Date: Jan. 13, 1993
[87] PCT Pub. No.: WO92/20297
  PCT Pub. Date: Nov. 26, 1992

[30] Foreign Application Priority Data

May 13, 1991 [DE] Germany .............. 4115961

[51] Int. Cl.⁶ ......................... F16B 23/00
[52] U.S. Cl. ................ 411/396; 411/383; 411/403; 411/408
[58] Field of Search ........ 411/403, 1, 5, 8, 383, 411/385, 914, 396, 408, 424, 910, 911, 919, 407

[56] References Cited

U.S. PATENT DOCUMENTS

| | | | |
|---|---|---|---|
| 2,058,197 | 10/1936 | West | 411/407 |
| 2,248,695 | 7/1941 | Bradshaw | 411/407 X |
| 2,631,624 | 3/1953 | Wright | 411/407 X |
| 3,298,273 | 1/1967 | McKelvey | 411/1 |
| 3,979,918 | 9/1976 | Vidler | 411/8 X |
| 4,793,808 | 12/1988 | Kirsch | |
| 4,824,372 | 4/1989 | Jorneus et al. | |
| 4,995,810 | 2/1981 | Soderberg | |

FOREIGN PATENT DOCUMENTS

| | | | |
|---|---|---|---|
| 0291103 | 11/1988 | European Pat. Off. | |
| 413224 | 12/1966 | Switzerland | |
| 920221 | 3/1963 | United Kingdom | 411/396 |
| 804892 | 2/1981 | U.S.S.R. | 411/366 |
| WO88/08283 | 11/1988 | WIPO | |

Primary Examiner—Rodney M. Lindsey
Attorney, Agent, or Firm—Hill, Steadman & Simpson

[57] ABSTRACT

Screw unit with a closing screw having a screw head for the aseptic closing of an internal thread of a member and an introduction post in firm, but detachable connection on the closing screw.

The detachable connection is formed by a tongue in an end of the post being received in a slot in the screw head which slot terminates inward of a peripheral edge of the screw head.

12 Claims, 2 Drawing Sheets

SCREW UNIT

BACKGROUND OF THE INVENTION

The invention relates to a screw unit with a closing screw having a screw slot for the aseptic closing of an internal thread, particularly for closing an internal thread in a member to be implanted in bone material for receiving an implant post or the like.

Enossal implants, i.e. members to be implanted in the jawbone, are e.g. known from EP 0 216 031 A1 and have proved extremely satisfactory in practice. During the implantation of such members absolute sterility must be ensured in order to keep the inflammation risk low. An implanted member must initially be engaged by the bone growth prior to the introduction of the implant post or the like. During this time the internal thread of the member is closed, because it would otherwise fillup with dead material, which cannot be transported away.

For introducing the member into the bone, it is conventional practice to improve its handling to screw an insertion post in the internal thread and the post is subsequently removed. The internal thread of the member is subsequently closed with a special closing screw. This screw is removed as soon as the bone has firmly grown onto the member and then an implant post, an implant extension, a post for attachments, etc. or a screw for fixing crowns and other structures in dental prosthetics will be screwed into the implanted member.

SUMMARY OF THE INVENTION

The object of the invention is to provide a possibility during implantation of a member of reliably and precisely handling the member which is provided with a closing screw for the internal thread and which is to be implanted in the bone.

According to the invention this problem is solved in that an introduction post is provided in a firm, but detachable seating on the closing screw. Such a post on which it is possible to act by means of a corresponding special tool, such as e.g. forceps, offers the possibility of a safe and precise handling of the member to be implanted. Following the introduction of the member it can be readily detached from the closing screw and removed. The internal thread remains aseptically closed throughout the entire surgical manipulation. The introduction post is then sterilized together with the screw and mains in its seating on the closing screw for the time necessary for handling the member.

A preferred construction of the inventive screw unit comprises the introduction post being in positive contact with the closing screw in the rotation direction and in frictional contact in the axial direction. This has the advantage that an almost randomly high force can be used in the rotation direction, whereas a relatively shall force is sufficient in the axial direction to release the introduction post from the connection to the closing screw.

It is also recommended to use a closing screw which has a screw slot, which terminates inward of the peripheral edge of the screw head and to provide the introduction post with at least one tongue on which is provided at least one outward bulge resting under clamping action in the screw slot on assembling the introduction post and the closing screw. As a result of such a screw slot and a tongue on the introduction post engaging therewith, it is possible in a particularly effective manner to bring about the desired frictional contact between the introduction post and the closing screw. Such a construction is also advantageous, because such a screw slot can also be used for the reliable application of a conventional screwdriver, such as is e.g. used for removing the screw from the implanted member after the bone has grown onto the implanted member. Thus, it is possible to reliably avoid a slipping off of the screwdriver and consequently any risk of the surrounding tissue being injured. Such a construction leads to no additional corners or edges, where possible inflammation could occur. In addition, a smooth, round outside of the screw is ensured, which does not excessively irritate the surrounding tissue. It is finally also impossible for the tissue to grow into the screw slot.

According to a preferred construction the tongue has a recess around the introduction post axis. As a result of the recess the outward bulge or bulges can cone into resilient, clamping contact with the ends of the screw slot.

It is also proposed to provide the recess with a V-shape. The V-shaped recess;

Has proved to be advantageous, because the two remaining portions of the tongue can in this way snap into the screw slot without any special demands having to be made on the material used for the tongue.

With respect to the construction of the outward bulge or bulges, it is proposed that they be provided with pressing edges, so that the outward bulge is given a trapezoidal shape in a section along the longitudinal extension of the tongue. Preferably a first edge passes from the tongue terminal or surface running at right angles to the introduction post axis to a second lateral edge running parallel to the introduction post axis and is connected there with a steep angle and a third edge passes from the lateral second edge with a shallow angle inwards to the attachment point of the tongue to the introduction poet. As a result of a much smaller bearing surface, namely only the lateral, second edge on the ends of the screw slot, such a construction simultaneously ensures an adequate frictional contact and a good detachability between the closing screw and the introduction post.

Preferably the ends of the screw slot are rounded, so that the frictional contact in this preferred embodiment of the invention occurs only at four points of the screw slot and accompanied by a simultaneous good clamping action a removal of the introduction post following the termination of the bone surgical manipulations is facilitated.

A major part is particularly played by the V-shaped recess, because only it provides an adequate resilience to the pressing edges or corners of the outward bulges on the tongue portions left behind. Together with the special shaping of the pressing edges of the outward bulge and possibly the screw slot, the possibility is provided, following a successful introduction of the member, to easily release the introduction post, i.e. by levering it out using tilting movements.

For the better handling of the introduction post, it is recommended that the post be provided with a hemispherical impact or striking head on its end remote from the closing screw. Thus, the head can consequently absorb blows striking it in an inclined manner for the further introduction of the member into the prepared bone.

It is also proposed that the introduction post be provided with a smaller radius handle portion located upstream of the striking head. It is possible to reliably apply to the said handle portion a corresponding special tool for handling the member to be implanted, such as e.g. forceps.

Adjacent to the closing screw preferably a widened portion is provided on the introduction post in order to prevent any slipping in the direction of the bone of the tool engaging on the handle portion.

Further features and advantages of the invention can be gathered from the following non-limitative description of an embodiment, the claims and the attached:

DESCRIPTION OF THE PREFERRED EMBODIMENTS

Figure 1:
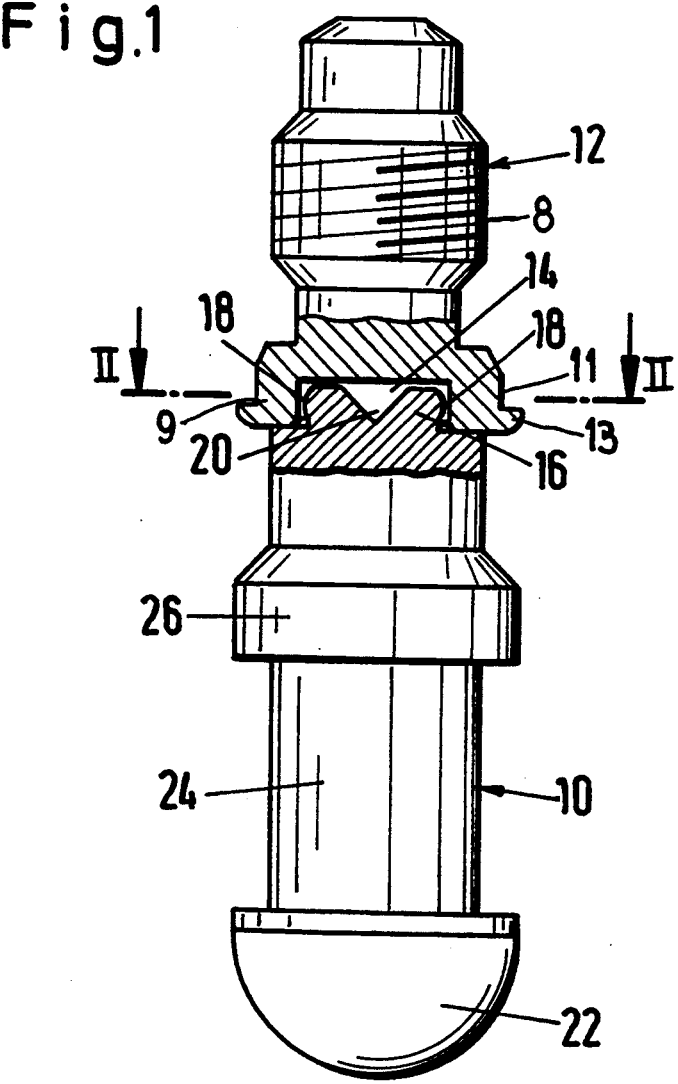
FIG. 1 is a side view with portions broken away of the closing screw assembled with an introduction post according to the present invention.

FIG. 1 shows a closing screw 12 with an inserted introduction post 10, in the way in which they are interconnected for implanting a member closed with a closing screw. The screw 12 has a portion with threads 8 and a screw head 9 with a peripheral surface 11 with a radial flange 13. The screw head of the closing screw 12 is provided with a screw slot 14, which terminates inward of the peripheral surface 11 instead of having a through construction. As has been explained hereinbefore, the slot 14 is used for receiving a tongue 16 on the introduction poet 10, which is provided with two outward bulges 18, between which there is a V-shaped recess 20, whose upper edges are curved or bent, in the manner shown in FIG. 2.

Figure 2:
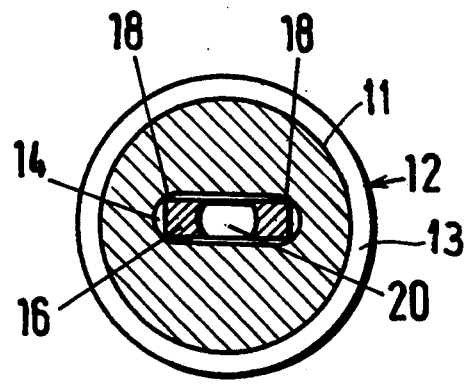
FIG. 2 is a cross sectional view taken on line A—A of FIG. 1.

The screw slot 14 in the head of the screw 12 is also provided with rounded ends 15, as can also be seen in FIG. 2, so that substantially them is only a frictional contact between the four corner points of the two outward bulges 18 of the tongue 16 and the screw slot 14. As a result of the V-shaped recess 20 between the two outward bulges 18, the tongue 16, which is preferably made from a material with corresponding elasticity characteristics, can snap into the screw slot 14 of the closing screw 12 and at the end of the bone surgical manipulations can in a simple manner easily be detached again from the firm seating on the closing screw 12.

FIG. 1 also shows a particularly preferred embodiment of the introduction post 10, which is provided on the end remote from the closing screw 12 with a hemispherical impact or striking head 22, which serves as an impact or striking surface, so that the member to be implanted can be driven further into the prepared bone and as a result of the hemispherical shape of the head 22 blows applied in an inclined manner can be absorbed. Extending from the striking head 22 in the direction of the closing screw 12, the post 10 is provided with a smaller radius handle portion 24. The portion 24 is used for the engagement of a special tool for handling the screw unit according to the invention and the tool may be in the form of forceps. The larger radius of the striking head 22 ensures that the corresponding special tool cannot slip upwards during handling. In order to also prevent a slipping downward and towards the member to be implanted and the surrounding bone and tissue material, a widened portion 26 is provided on the introduction post 10 adjacent to the tongue 16.

Figure 3:
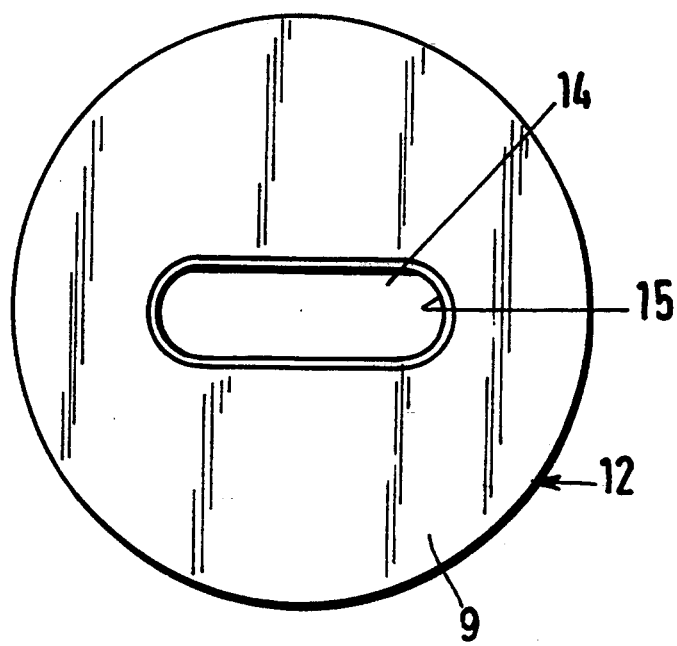
FIG. 3 is a plan view of the head of the closing screw.

FIG. 3 again shows in plan view the screw slot 14 in the head 9 of the screw 12 and it is particularly easy to see the rounded ends 15 thereof.

Figure 4:
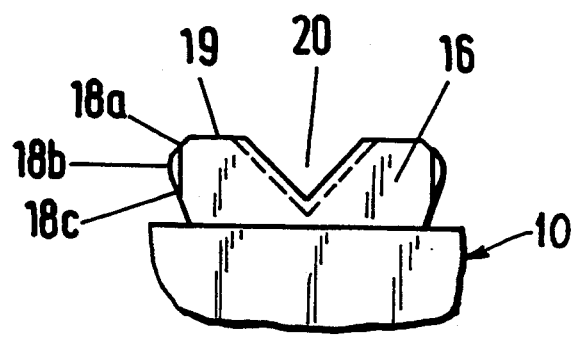
FIG. 4 is an enlarged partial side view of an end of the introduction post with the tongues.

The trapezoidal shape of the outward bulges 18 by the arrangement of pressing edges 18a, 18b and 18c of the tongue 16 with respect to one another and relative to their terminal edge or surface 19 is shown in FIG. 4, which is a much larger-scale detail of FIG. 1 with respect to tongue 16. The edge 18a in particular has a guidance function on the assembly of the two parts of the inventive screw unit, namely the introduction post 10 and the closing screw 12. The relatively short edge 18b makes it possible to relatively easily separate the introduction poet 10 from the closing screw 12 by carrying out tilting movements of the post 10 relative to the screw 12 in the direction of the screw slot 14 and as a result the tongue 16 is released from the screw slot 14.

As a result of the thus described introduction post 10, which can be sterilized together with the member terminated by the closing screw, a possibility is provided to easily orient the entire member to be implanted, as well as the closing screw 12 during implanting and without requiring additional manipulations of the screw 12 or the member to be implanted.

The features of the invention disclosed in the above description, in the drawings and claims can be essential to the realization of the different embodiments of the invention either singly or in the form of random combinations.

We claim:

1. In a screw unit with a closing screw with a screw head for the aseptic closing of an internal thread in a member to be implanted in a bone material, the improvement comprising an elongated introduction post with a longitudinal axis having one end forming a firm, detachable connection with the closing screw, said detachable connection providing a positive contact between the post and the closing screw in the rotation direction and a frictional contact therewith in the axial direction, said detachable connection being formed by the screw head having an elongated screw slot, which terminates inward of a peripheral edge of the screw head, and the introduction post being provided with at least one tongue at said one end, said tongue having an elongated cross section with at least one outward bulge having pressing edges and a trapezoidal shape in a section along a longitudinal extension of the tongue, said tongue with the bulge resting under clamping action in the screw slot, when the introduction post and the closing screw are assembled.

2. In a screw unit according to claim 1, wherein a first edge of the pressing edges passes from the terminal edge of the tongue which is at right angles to the longitudinal axis of the introduction post to a second lateral edge running parallel to the longitudinal axis of the introduction post and is connected thereto by a steep angle and a third edge passes from the lateral second edge inward at a shallow angle to an attachment point of the tongue to the introduction post.

3. In a screw unit according to claim 2, wherein the screw slot has rounded ends.

4. In a screw unit with a closing screw with a screw head for aseptic closing of an internal thread in a member to be implanted in bone material, the improvement comprising an elongated introduction post with longitudinal axis having one end forming a firm, detachable connection to the closing screw, said detachable connection being formed by the screw head having an elongated slot with rounded ends of the slot being spaced inward of a peripheral edge of the screw head, and said one end of the post having a tongue extending along a longitudinal axis of the post, said tongue having a substantially V-shaped recess around the longitudinal axis of the introduction post and an elongated cross section with at least one outward bulge, said connection being formed by the tongue being received in the slot with positive contact for transferring rotary movement of the post to the screw and frictional contact within a direction parallel to the longitudinal axis of the post, said bulge providing a clamping action when the tongue is in said slot.

5. In a screw unit according to claim 4, wherein a second end of the introduction post remote from the one end and closing screw is provided with a hemispherical striking head.

6. In a screw unit according to claim 5, wherein the introduction post has a smaller radius handle portion located between the striking head and the one end with the tongue.

7. In a screw unit according to claim 6, wherein a widened portion is provided on the introduction post adjacent to the closing screw to space the tongue from the handle portion.

8. In a screw unit with a closing screw with a screw head for aseptic closing of an internal thread in a member to be implanted in a bone material, the improvement comprising an elongated introduction post having one end forming a firm, detachable connection to the closing screw, said detachable connection being formed by the screw head having a slot with a rectangular shape with ends of the slots being spaced inward of a peripheral edge of the screw head, and said one end of the post having a tongue extending along a longitudinal axis of the post, said tongue having a shape substantially the same as said slot and being provided with at least one outward bulge, the outward bulge being provided with pressure edges with a first edge of the pressure edges passing from a terminal edge of the tongue, which is at a right angle to the longitudinal axis of the introduction post, to a second lateral edge running parallel to the longitudinal axis of the introduction post and being connected thereto by a steep angle and a third edge passing from the second lateral edge inward at a shallow angle to an attachment point of the tongue to the introduction post, so that in a section along the longitudinal extension of the tongue, the bulge has a trapezoidal shape, said connection being formed by the tongue being received in the slot with positive contact for transferring rotary movement of the post to the screw and frictional contact within a direction parallel to the longitudinal axis of the post, said bulge providing a clamping action when the tongue is in said slot.

9. In a screw unit according to claim 8, wherein the tongue has a V-shaped recess on the longitudinal axis of the post, said ends of said slot being rounded ends to form a four-point contact with the tongue.

10. In a screw unit according to claim 8, wherein the introduction post has a second end opposite the one end, said second end being provided with a hemispherical striking head.

11. In a screw unit according to claim 10, wherein the introduction post has a flange adjacent the one end to provide a small radius handle portion between the striking head and said flange.

12. In a screw unit with a closing screw with a screw head for the aseptic closing of an internal thread in a member to be implanted in a bone material, the improvement comprising an elongated introduction post with a longitudinal axis having one end forming a firm, detachable connection with the closing screw, the detachable connection being formed by the head of the screw having an elongated slot which terminates inward of a peripheral edge of the head with rounded ends, said slot receiving a resilient tongue on an end of the post with contact only at four points so that rotation of the post is transferred to the screw.

* * * * *